US00PP14859P2

(12) United States Plant Patent
Hooijman

(10) Patent No.: US PP14,859 P2
(45) Date of Patent: Jun. 1, 2004

(54) HYPERICUM PLANT NAMED 'ESMFIRE'

(50) Latin Name: *Hypericum androsaemum*
Varietal Denomination: Esmfire

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 10/637,053

(22) Filed: Aug. 7, 2003

(51) Int. Cl.[7] ..... A01H 5/00
(52) U.S. Cl. ..... Plt./226
(58) Field of Search ..... Plt./226, 263

(56) References Cited

PUBLICATIONS

UPOV–ROM GTITM, Plant Variety Database, 2003/05, GTI Jouve Retrieval Software, Citation for Hypericum 'Esmfire'.*

* cited by examiner

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of Hypericum plant named 'Esmfire', characterized by its upright plant habit; dark green-colored leaves; large red purple-colored fruits; and good postproduction longevity.

1 Drawing Sheet

Botanical classification/cultivar designation: *Hypericum androsaemum* cultivar Esmfire.

BACKGROUND OF THE INVENTION

The present Invention relates to a new and distinct cultivar of Hypericum plant, botanically known as *Hypericum androsaemum,* commercially used as cut stems with fruits, and hereinafter referred to by the name 'Esmfire'.

The new Hypericum is a product of a planned breeding program conducted by the Inventor in El Quinche, Pichincha, Ecuador. The objective of the breeding program was to develop cut Hypericum varieties with large fruit and attractive coloration.

The new cultivar originated from a cross-pollination made by the Inventor in August, 1999 of a proprietary selection of *Hypericum androsaemum* identified as Code 02, not patented, as the female, or seed, parent with an unidentified selection of *Hypericum androsaemum,* not patented, as the male, or pollen, parent. The cultivar Esmfire was discovered and selected by the Inventor as a flowering plant within the progeny of the stated cross-pollination in a controlled environment in El Quinche, Pichincha, Ecuador.

Asexual reproduction of the new Hypericum by terminal cuttings taken at El Quinche, Pichincha, Ecuador since June, 2000, has shown that the unique features of this new Hypericum are stable and reproduced true to type in successive generations of asexual reproduction.

SUMMARY OF THE INVENTION

The following traits have been repeatedly observed and are determined to be the unique characteristics of 'Esmfire'. These characteristics in combination distinguish 'Esmfire' as a new and distinct cultivar:

1. Upright plant habit.
2. Dark green-colored leaves.
3. Large red purple-colored fruits.
4. Good postproduction longevity.

Plants of the new Hypericum differ from plants of the female parent selection identified as Code 02 in the following characteristics:

1. Plants of the new Hypericum are shorter than plants of the female parent selection.
2. Plants of the new Hypericum have lighter green-colored leaves than plants of the female parent selection.
3. Plants of the new Hypericum have more rounded fruits than plants of the female parent selection.
4. Plants of the new Hypericum and the female parent selection differ in fruit coloration.

Plants of the new Hypericum differ from plants of the male parent selection primarily in fruit size and coloration.

Plants of the new Hypericum can be compared to plants of the Hypericum cultivar Bosapin, disclosed in U.S. Plant Pat. No. 10,993. In side-by-side comparisons conducted in El Quinche, Pichincha, Ecuador, plants of the new Hypericum differed from plants of the cultivar Bosapin in the following characteristics:

1. Plants of the new Hypericum had broader and lighter green-colored leaves than plants of the cultivar Bosapin.
2. Plants of the new Hypericum had more rounded fruits than plants of the cultivar Bosapin.
3. Plants of the new Hypericum and the cultivar Bosapin differed in fruit coloration.

BRIEF DESCRIPTION OF THE PHOTOGRAPHS

The accompanying colored photographs illustrate the overall appearance of the new Hypericum, showing the colors as true as it is reasonably possible to obtain in colored reproductions of this type. Colors in the photographs may differ slightly from the color values cited in the detailed botanical description which accurately describe the colors of the new Hypericum.

The photograph at the top of the sheet comprises a side perspective view of a typical stem of 'Esmfire' in fruit.

The photograph at the bottom of the sheet is a close-up view of a typical cluster of fruits, the upper surface of a typical leaf, and the lower surface of a typical leaf of 'Esmfire'.

DETAILED BOTANICAL DESCRIPTION

The new Hypericum has not been observed under all possible environmental conditions. The phenotype may vary somewhat with variations in environment such as temperature, daylength and light intensity, without, however, any variance in genotype.

The aforementioned photographs, following observations and measurements describe plants grown in El Quinche, Pichincha, Ecuador, in an outdoor nursery and under commercial production practices. Plants were about one year old. During the production of the plants, day temperatures ranged from 12 to 30° C. and day temperatures ranged from 5 to 12° C. Plants were pinched about two weeks after planting. In the following description, color references are made to The Royal Horticultural Society Colour Chart, 2001 Edition, except where general terms of ordinary dictionary significance are used.

Botanical classification: *Hypericum androsaemum* cultivar Esmfire.

Parentage:

*Female parent.*—Proprietary selection of *Hypericum androsaemum* identified as Code 02, not patented.

*Male parent.*—Unidentified selection of *Hypericum androsaemum,* not patented.

Propagation:

*Type.*—Terminal cuttings.

*Time to initiate roots.*—About 7 to 10 days at 22 to 30° C.

*Time to produce a rooted cutting.*—About 28 to 35 days at 22 to 30° C.

*Root description.*—Fibrous, fine; color, 167A.

*Rooting habit.*—Freely branching, dense.

Plant description:

*Plant form.*—Upright and somewhat outwardly spreading perennial woody shrub; erect inverted triangle.

*Growth habit.*—Moderately vigorous. Freely basal branching; dense and bushy growth habit.

*Plant height.*—About 78 cm.

*Plant width* (*spread*).—About 25.8 cm.

*Quantity of stems per year.*—About 12; production of stems increases with age of plants.

*Lateral branches.*—Length: About 78 cm. Diameter: About 6 mm. Internode length: About 5.9 cm. Strength: Strong. Texture: Smooth; glabrous. Color: 181D.

*Foliage description.*—Arrangement: Opposite, simple; sessile. Length: About 7.5 cm. Width: About 5.6 cm. Shape: Oval to lanceolate. Apex: Acute. Base: Cordate. Margin: Entire. Texture, upper and lower surfaces: Glabrous; smooth. Venation pattern: Pinnate. Color: Developing leaves, upper surface: 144A. Developing leaves, lower surface: 138B. Fully expanded leaves, upper surface: 137A. Fully expanded leaves, lower surface: 138B. Venation, upper surface: 144C. Venation, lower surface: 157A.

Flower description:

*Flower type and habit.*—Bright yellow single flowers arranged in terminal compound umbels with about 15 flowers per lateral branch. Flowers fragrant. Flowers not persistent. Flowers face upright.

*Natural flowering season.*—Summer, typically July through early September in The Netherlands; flowering period typically lasts about 60 days.

*Postproduction longevity.*—Cut stems are typically harvested when all flowers have developed fruits. Flowers last about three days on the plant. Postproduction longevity of cut stems with fruits about 14 to 18 days.

*Inflorescence height.*—About 11.2 cm.

*Inflorescence diameter.*—About 8.9 cm.

*Flower buds.*— Height: About 1 cm. Diameter: About 7 mm. Shape: Ovoid. Color: Towards the apex, 13A; towards the base, 13C.

*Flowers.*—Diameter: About 2.8 cm. Depth: About 1.4 cm.

*Petals.*—Quantity per flower: Typically five. Length: About 1.3 cm. Width: About 1 cm. Shape: Oval. Aspect: Incurved. Apex: Rounded. Base: Attenuate. Margin: Entire. Texture, upper and lower surfaces: Smooth, glabrous. Color: Developing and fully expanded petals, upper surface: 13B. Developing and fully expanded petals, lower surface: 12A.

*Sepals.*—Quantity per flower: Typically five. Length: About 1 cm. Width: About 8 mm. Shape: Oval. Apex: Acute to rounded. Base: Rounded. Margin: Entire. Texture, upper and lower surfaces: Smooth, glabrous. Color: Developing sepals, upper surface: 144A overlain with 60A. Developing sepals, lower surface: 148B overlain with 53A. Fully developed sepals, upper surface: 144A. Fully developed sepals, lower surface: 138B.

*Peduncles.*—Length: About 5.8 cm. Diameter: About 2 mm. Orientation: Erect to about 35° from vertical. Strength: Strong to moderately strong. Color: 178B.

*Pedicels.*—Length: About 1.4 cm. Diameter: About 1.8 mm. Orientation: Erect to about 55° from vertical. Strength: Moderately strong. Color: N144C.

*Reproductive organs.*—Stamens: Quantity per flower: About 82. Anther shape: Oval. Anther length: About 0.7 mm. Anther color: 23A. Pollen amount: Scarce. Pollen color: 23A. Pistils: Quantity per flower: Typically three. Pistil length: About 1.4 cm. Stigma shape: Globular. Stigma color: 59A. Style length: About 8 mm. Style color: 2C. Ovary color: 1B.

*Fruits.*—Quantity per flower: One. Days to ripening: About 52 to 56. Type: Capsule. Shape: Ellipsoidal. Length: About 11.6 mm. Diameter: About 8.7 mm. Texture: Smooth, glabrous. Color: 50A.

*Seeds.*—Length: About 1.3 mm. Diameter: About 0.4 mm. Texture: Smooth, glabrous. Color: N119B.

Disease/pest resistance: Plants of the new Hypericum have not been observed to be resistant to pests common to Hypericum. Plants of the new Hypericum have been observed to be slightly resistant to rust pathogens.

Temperature tolerance: Plants of the new Hypericum have been observed to tolerate temperatures ranging from 0 to 30° C.

It is claimed:

1. A new and distinct cultivar of Hypericum plant named 'Esmfire', as illustrated and described.

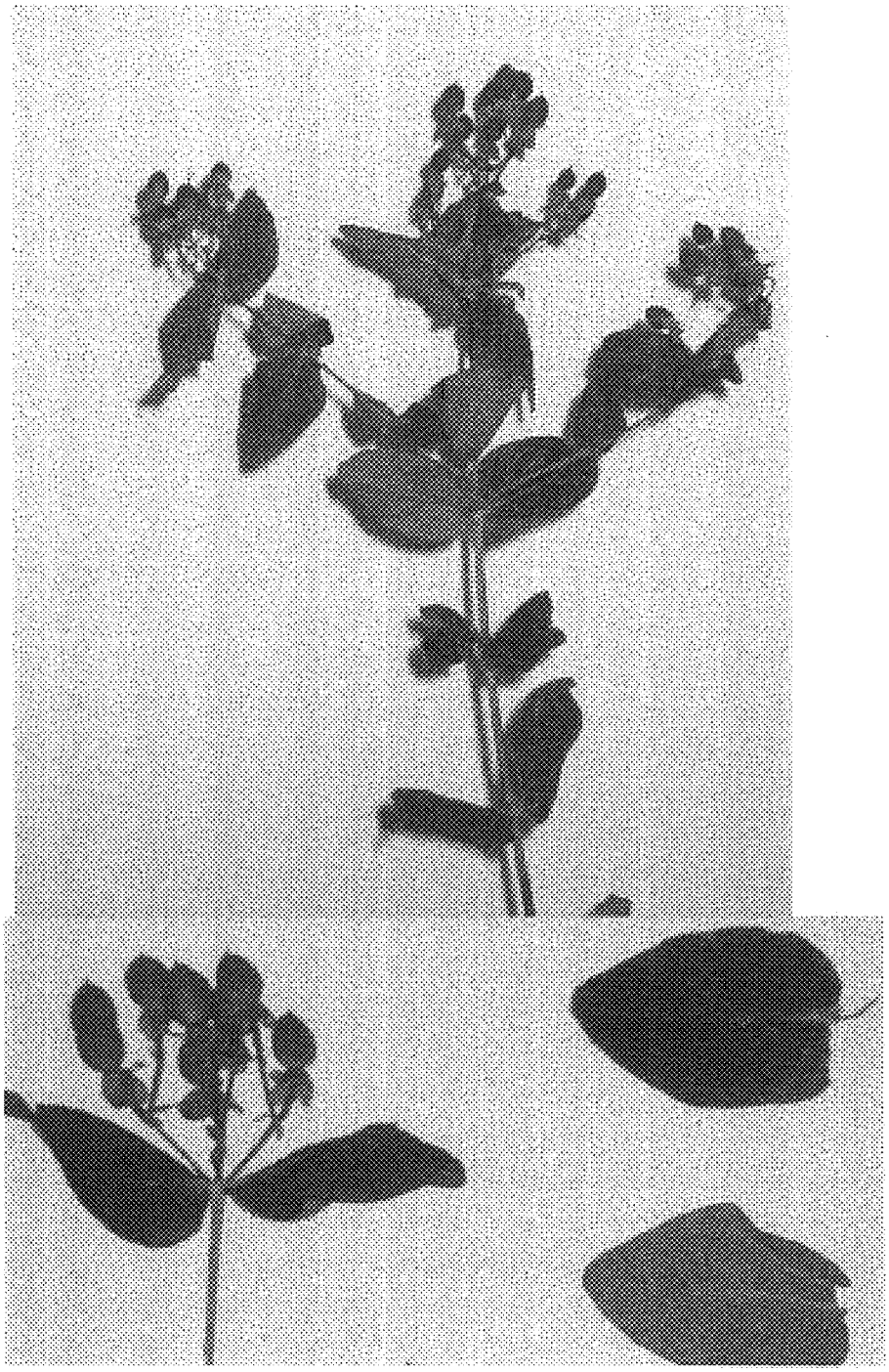

* * * * *